United States Patent [19]  [11] 4,134,909
Pigerol et al. [45] Jan. 16, 1979

[54] 3-METHOXY-4-ARYLSULPHONYLOXY-ACETOPHENONES

[75] Inventors: Charles Pigerol, Saint-Ouen; Paul de Cointet de Fillain, Sisteron; Yves Bazile, Sisteron; Michel Chignac, Sisteron; Claude Grain, Volonne, all of France

[73] Assignee: Labaz, Paris, France

[21] Appl. No.: 811,054

[22] Filed: Jun. 29, 1977

[30] Foreign Application Priority Data

Jul. 15, 1976 [FR] France .................. 76 21581

[51] Int. Cl.² ................. C07C 143/68; C08K 5/10
[52] U.S. Cl. .................... 260/456 P; 260/45.7 S; 260/326.16
[58] Field of Search ................. 260/456 P

[56] References Cited

U.S. PATENT DOCUMENTS 3,818,102  6/1974  Partos ............... 260/456 P

Primary Examiner—Joseph E. Evans
Attorney, Agent, or Firm—Mason, Kolehmainen, Rathburn & Wyss

[57] ABSTRACT

The invention relates to new compounds of the general formula :

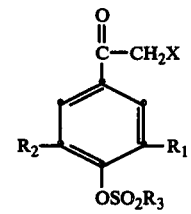

wherein X represents a hydrogen or halogen atom, $R_1$ and $R_2$, which are the same or different, each represent a hydrogen atom or a methoxy radical and $R_3$ represents an alkyl or aryl radical, with the proviso that at least one of the substituents $R_1$ and $R_2$ is not a hydrogen atom.

The compounds of formula I are useful for preparing stabilizers for thermoplastic resins.

9 Claims, No Drawings

3-METHOXY-4-ARYLSULPHONYLOXY-ACETOPHENONES

The present invention relates to new acetophenone derivatives, to a process for preparing said acetophenone derivatives and to their methods of use.

The acetophenone derivatives with which the present invention is concerned are the compounds represented by the formula:

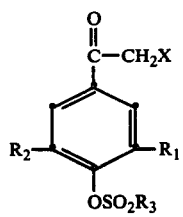
I wherein X represents a hydrogen or halogen atom such as, for instance, a bromine or chlorine atom, $R_1$ and $R_2$, which are the same or different, each represent a hydrogen atom or a methoxy radical and $R_3$ represents an alkyl or aryl radical such as, for instance, a methyl, phenyl or p-tolyl radical with the proviso that at least one of the substituents $R_1$ and $R_2$ is not a hydrogen atom.

The present invention relates also to the process for preparing the compounds of formula I, whereby an acetophenone derivative represented by the formula:

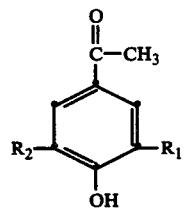
II wherein $R_1$ and $R_2$ have the same meanings as in formula I, is reacted with an alkyl-sulphonyl or arylsulphonyl chloride, in the presence of sodium hydroxide, to give a compound of formula I, wherein X represents a hydrogen atom, which may be reacted with chlorine or bromine, in the presence of methanol, to give a compound of formula I, wherein X represents a chlorine or bromine atom.

The compounds of formula II are known, having been described by BRADLEY and ROBINSON in J. Chem. Soc. 2362 (1926) and 1564 (1928), or can be prepared by well-known methods.

The compounds of formula I have been found to be useful as starting-products for preparing 2-phenylindole derivatives represented by the general formula:

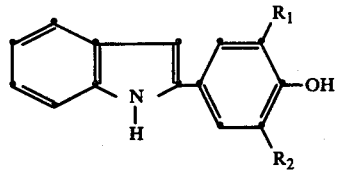
III wherein $R_1$ and $R_2$ have the same meanings as in formula I.

The compounds of formula III are very valuable stabilizing agents for polymers and co-polymers of vinyl chloride.

The present invention furthermore relates to the methods of use of the compounds of formula I, which consist in transforming a compound of formula I into the corresponding compound of formula III by the FISCHER or BISCHLER indole synthesis.

One method of use of the compounds of formula I, wherein X represents a hydrogen atom, consists in reacting, according to FISCHER, the said compound of formula I with phenylhydrazine to give an acetophenone phenylhydrazone of the general formula:

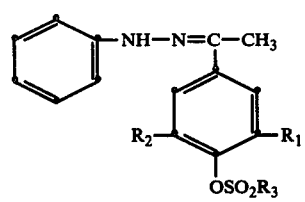
IV wherein $R_1$, $R_2$ and $R_3$ have the same meanings as in formula I, and cyclising the compound of formula IV by means of a dehydrating agent such as, for instance, polyphosphoric or sulphuric acid, to give a 2-phenylindole derivative of the general formula:

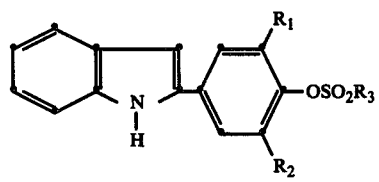
V wherein $R_1$, $R_2$ and $R_3$ have the same meanings as in formula I, and finally saponifying the compound of formula V, in an alkaline medium, to give the desired compound of formula III.

Another method of use of a compound of formula I, wherein X represents a halogen atom, consists in reacting, according to BISCHLER, the said compound of formula I with aniline to give a compound of the above formula V and saponifying the latter, in an alkaline medium, to provide the desired compound of formula III.

Up to present, the compounds of formula III have been prepared by the same FISCHER and BISCHLER methods but starting from a compound of formula II or a halogenated derivative thereof.

Said methods, however, do not give good results, mainly because of the presence in the 4-position of the acetophenone of a hydroxy radical, an electrodonor group which renders both the FISCHER and the BISCHLER reactions difficult to achieve.

For instance, the FISCHER Indole Synthesis, when applied to a compound of formula II, gives the corresponding stabilizer of formula III with a total yield of at most 50%, whereas the same method, when applied to a compound of formula I, enables the corresponding stabilizer of formula III to be obtained with a total yield of 70%, in spite of the fact that two additional steps are involved.

In the case of the BISCHLER Indole Synthesis, the difference between the yields is even more marked. Thus, this method, when applied to a halogenated derivative of a compound of formula II gives a yield which does not reach 20%, whereas a yield of 60% is obtained when starting from a compound according to the invention.

The compounds of the invention represent therefore a particularly valuable means of obtaining on the industrial scale stabilizers for thermoplastic resins.

It is however understood that the compounds of the invention could also be used for preparing other 2-phenyl-indole derivatives than those of formula III.

The following Examples provide a non-limitative illustration of the process of preparation of the compounds of the invention and of their methods of use:

EXAMPLE 1

3-Methoxy-4-benzenesulphonyloxy-acetophenone

Into a reactor were introduced 900 ml of water containing 44 g (1.1 mol) of sodium hydroxide and 166 g (1 mol) of 3-methoxy-4-hydroxyacetophenone.

The mixture was heated to 40°-45° C. and 194 g (1.1 mol) of benzene sulphochloride were added in two hours. The acetophenone precipitated and, after cooling of the medium, was filtered off and washed with purified water to neutrality.

The 3-methoxy-4-benzenesulphonyloxy-acetophenone so obtained was dried and directly used for preparing 2-phenyl-indole derivatives.

Melting point: 88° C. Yield: 99%

EXAMPLE 2

3,5-Dimethoxy-4-benzenesulphonyloxy-acetophenone

Into a reactor were introduced 1000 ml of 1,2-dichloroethane, 196 g (1 mol) of 3,5-dimethoxy-4-hydroxy-acetophenone and 151.5 g (1.5 mol) of triethylamine. The mixture was stirred until a homogeneous solution was obtained and, while stirring, 265 g (1.5 mol) of benzenesulphochloride were added in one hour. The temperature of the medium reached 40° C. and was maintained at that temperature for one hour. The mixture was poured into water and the 3,5-dimethoxy-4-benzenesulphonyloxyacetophenone precipitated, was filtered off, washed with water to neutrality and finally washed with ether.

The 3,5-dimethoxy-4-benzenesulphonyloxy-acetophenone was dried and directly used for preparing 2-phenyl-indole derivatives.

Melting point: 96° C. Yield: 99%

EXAMPLE 3

3-Methoxy-4-methylsulphonyloxy-acetophenone

While stirring, 2.7 liters of water and 132 g of sodium hydroxide were introduced into a reactor maintained at 25° C. and 498 g (3 mols) of 3-methoxy-4-hydroxy-acetophenone were progressively added. While stirring and at a temperature of 20° C., 378.2 g of methanesulphochloride were added in two hours.

The mixture was stirred for 30 minutes and 30 g of solid sodium hydroxide were added, followed by 34 g of methanesulphochloride. The mixture was stirred for one hour, was dried on a Buchner funnel and was washed with water until elimination of the chloride ions. The product was dried under vacuum in an oven at 40° C. for 12 hours and 694 g of 3-methoxy-4-methylsulphonyloxy-acetophenone were obtained.

Melting point: 90° C. Yield: 94%

EXAMPLE 4

3-Methoxy-4-toluenesulphonyloxy-acetophenone

Into a reactor were introduced 332 g (2 mols) of 3-methoxy-4-hydroxy-acetophenone, 1.8 liter of water and 88 g of solid sodium hydroxide. The temperature of the reaction medium increased and was maintained at about 70° C. In 90 minutes were added 419.3 g (2.2 mols) of molten toluenesulphochloride, at a temperature of 65°-70° C. and, while stirring for 30 minutes, the reaction medium was allowed to cool to room temperature. 24 g of sodium hydroxide were added and the reaction medium was allowed to cool to room temperature. The precipitate was dried on a Buchner funnel and was washed with water until elimination of the chloride ions.

The product was dried in an oven at 40° C. for 12 hours and 622 g of 3-methoxy-4-toluenesulphonyloxy-acetophenone were obtained.

Melting point: 89° C. Yield: 97%

EXAMPLE 5

3-Methoxy-4-benzenesulphonyloxy-ψ-chloroacetophenone (a) Preparation of 1-benzenesulphonyloxy-2-methoxy-4-(1′,1′-dimethoxy-2′-chloro-ethyl)-benzene Into a reactor were introduced 1 liter of methanol and 229.5 g (0.75 mol) of 3-methoxy-4-benzenesulphonyloxy-acetophenone, prepared as in Example 1, and the mixture was refluxed. In 90 minutes were added 58.9 g (0.83 mol) of chlorine and reflux was continued under vigorous stirring. The reaction medium was progressively cooled to room temperature and then to −10° C.

The precipitate obtained was purified by washing with methanol to give 1-benzenesulphonyloxy-2-methoxy-4-(1′,1′-dimethoxy-2′-chloroethyl)-benzene.

Melting point: 130° C. Yield: 85%

(b) Preparation of 3-methoxy-4-benzenesulphonyloxy-ω-chloroacetophenone

Into a reactor were successively introduced 660 ml of water, 66 ml of 36% sulphuric acid and 255 g (0.66 mol) of 1-benzenesulphonyloxy-2-methoxy-4-(1′,1′-dimethoxy-2′-chloro-ethyl)-benzene and the reaction medium was refluxed. After cooling to 40° C., 560 ml of toluene were added and, the temperature being maintained at the same level, the toluenic phase was decanted, washed with water to neutrality and dried.

The toluenic solution was cooled to 0° C. and as soon as a precipitate formed, 1.3 liter of heptane was added and the reaction medium was cooled to −10° C.

The precipitate was filtered off and purified by washing with heptane to give 3-methoxy-4-benzenesulphonyloxy-ω-chloroacetophenone.

Melting point: 83° C. Yield: 95–98%.

EXAMPLE 6

3-Methoxy-4-toluenesulphonyloxy-ω-chloroacetophenone (a) Preparation of
1-toluenesulphonyloxy-2-methoxy-4-(1',1'-dimethoxy-2'-chloro-ethyl)-benzene Into a reactor heated to 64° C. were dissolved 240 g (0.75 mol) of 3-methoxy-4-toluenesulphonyloxy-acetophenone in 1030 ml of methanol. As soon as the medium was homogeneous, 58.5 g (0.82 mol) of chlorine were introduced in 90 minutes, the temperature being maintained at 64-65° C.

The reaction medium was cooled to 20° C. in a water-bath and a precipitate formed. The reaction medium was cooled to − 10° C. and maintained at that temperature for 1 hour. The precipitate was suction-filtered and dried in an oven at 40° C. for 12 hours to give 194 g of 1-toluenesulphonyloxy-2-methoxy-4-(1',1'-dimethoxy-2'-chloro-ethyl)benzene, which was directly engaged in the following step, without being analysed.

Yield: 64%

(b) Preparation of
3-methoxy-4-toluenesulphonyloxy-ω-chloroacetophenone

Into a reactor were introduced 194 g of 1-toluenesulphonyloxy-2-methoxy-4-(1',1'-dimethoxy-2'-chloro-ethyl)-benzene, 480 ml of water and 48 ml of 96% sulphuric acid.

The mixture was refluxed under vigorous stirring and the methanol which formed was continuously distilled off until a constant temperature of about 100° C. was obtained.

The molten substance was washed with water at 90°-95° C. and the reaction medium was allowed to cool slowly to 20° C., while the oily product was vigorously stirred in water until precipitation. The precipitate was suction-filtered and dried in a ventilated oven at 40° C. for 15-16 hours to give 171 g of 3-methoxy-4-toluenesulphonyloxy-ω-chloroacetophenone.

Melting point: 110°-112° C. Yield: 64%

EXAMPLE 7

3-Methoxy-4-methylsulphonyloxy-ω-chloroacetophenone (a) Preparation of
1-methylsulphonyloxy-2-methoxy-4-(1',1'-dimethoxy-2'-chloro-ethyl)-benzene While stirring and under nitrogen atmosphere were introduced into a reactor 1.78 liter of methanol and 414.8 g (1.7 mol) of 3-methoxy-4-methylsulfonyloxy-acetophenone and the reaction medium was refluxed until complete dissolution. While maintaining the reflux, 132.8 g of chlorine were introduced in 140 minutes. The reaction medium was cooled to 20° C. while stirring and then to − 10° C. for one hour. The precipitate which formed was suction-filtered and dried at 40° C. for 12 hours to give 331 g of a mixture of 1-methylsulphonyloxy-2-methoxy-4-(1',1'-dimethoxy-2'-chloro-ethyl)-benzene and 3-methoxy-4-methylsulphonyloxy-ω-chloroacetophenone, in a ratio of 20-80.

The melting point of the mixture was not easy to determine and lay between 97°-102° C.

(b) Preparation of
3-methoxy-4-methylsulphonyloxy-ω-chloroacetophenone

Into a reactor were introduced 328 g of the mixture obtained above, 1 liter of water and 100 ml of 96% sulphuric acid. The reaction medium was refluxed and the methanol formed was continuously distilled off until a constant temperature of 100° C. was obtained.

An oily product, of greater density than water, was obtained, was separated off and washed with water at 90°-95° C.

The reaction medium was allowed to cool and a precipitate was obtained, was suction-filtered and dried at 40° C. to give 264 g of 3-methoxy-4-methylsulphonyloxy-ω-chloroacetophenone.

Melting point: 104°-106° C. Yield: 56%

EXAMPLE 8

3-Methoxy-4-benzenesulphonyloxy-ω-bromoacetophenone (a) Preparation of
1-benzenesulphonyloxy-2-methoxy-4-(1',1'-dimethoxy-2'-bromo-ethyl)-benzene Into a reactor were introduced 612 g (2 mols) of 3-methoxy-4-benzenesulphonyloxy-acetophenone, 2.5 liters of methanol and, while stirring, the mixture was heated to 50° C. and 328 g (2.05 mols) of bromine were added in 1 hour.

The reaction medium was cooled in a cold water-bath and the precipitate which formed was suction-filtered washed with cool methanol and then dried at 40° C.

818 g of 1-benzenesulphonyloxy-2-methoxy-4-(1',1'-dimethoxy-2'-bromo-ethyl)-benzene were obtained.

Melting point: 134° C. Yield: 95%

(b) Preparation of
3-methoxy-4-benzenesulphonyloxy-ω-bromoacetophenone

Into a reactor were introduced 818 g of the above product, 1.1 liter of water and 110 ml of 96% sulphuric acid.

The reaction medium was progressively heated to reflux, while the methanol formed was distilled off, until a constant temperature of 100° C. was obtained.

The oily product which formed was decanted and washed with water at 90°-95° C. to neutrality.

The medium was crystallized by cooling and the precipitate was suction-filtered and dried at 40° C. to give 734 g of 3-methoxy-4-benzenesulphonyloxy-ω-bromoacetophenone.

Melting point: 90°-91° C. Yield: 95.5%

EXAMPLE 9

3-Methoxy-4-benzenesulphonyloxy-ω-chloroacetophenone

Into a reactor were introduced 72.8 g of methanol and, while stirring, 23 g (0.07 mol) of 3-methoxy-4-benzenesulphonyloxy-acetophenone. The mixture was refluxed until a homogeneous solution was obtained which was allowed to cool to a temperature of 46° C. ± 2° C. The reaction medium was placed under nitrogen atmosphere and, while maintaining the same temperature, 5.4 g of chlorine were added in 30 minutes. After the chlorine was added, the reaction medium was placed under nitrogen atmosphere for 15 minutes. The methanol was eliminated by partial distillation until a distillate of 54 g was obtained. 56.6 g of purified water were introduced into the reactor and the elimination of methanol was continued until a temperature of 98°–100° C. was reached at the head of the column. A distillate of 34 g of a mixture of methanol and water was obtained. 66.4 g of toluene were added to the reaction medium and, while stirring, the temperature was maintained at about 75° C.

The mixture was decanted and the lower aqueous phase was eliminated. The reaction medium was washed twice with 42 g of purified water at 75° C., the lower aqueous phase being eliminated each time.

The toluene was distilled off, first under atmospheric pressure and then under a pressure of 150 mm of Hg and a distillate of 63.5 g of toluene was obtained.

The 3-methoxy-4-benzenesulphonyloxy-ω-chloroacetophenone was poured onto a stainless-steel plate heated to 70° C., which was placed in a ventilated oven at 20° C. in order to facilitate crystallization. 25.6 g of 3-methoxy-4-benzenesulphonyloxy-ω-chloroacetophenone were obtained.

Melting point: 83° C. Yield: 100%

EXAMPLE 10

2-(3'-Methoxy-4'-benzenesulphonyloxy-phenyl)-indole (a) Preparation of 3-methoxy-4-benzenesulphonyloxy-acetophenone phenylhydrazone Into a reactor equipped with a Dean-Stark separator were introduced 100 ml of benzene, 1 ml of acetic anhydride, 10.8 g (0.1 mol) of phenylhydrazine and 30.6 g (0.1 mol) of 3-methoxy-4-benzenesulphonyloxyacetophenone prepared as in Example 1.

While stirring, the reaction medium was refluxed and the benzene solution was concentrated under reduced pressure. The phenylhydrazone precipitated and was directly engaged in the following step, without purification or analysis.

Yield: 100%

However, a sample was recrystallized from methanol and a melting point of 136° C. was registered.

By the same method, but using the appropriate starting-product, 3,5-dimethoxy-4-benzenesulphonyloxy-acetophenone was also prepared.

Melting point: 168° C.

(b) Preparation of 2-(3'-methoxy-4'-benzenesulphonyloxy-phenyl)-indole

Into a reactor were introduced 100 g of polyphosphoric acid, prepared by mixing four parts of phosphoric anhydride and six parts of orthophosphoric acid and, while stirring and in 15 minutes, 20 g (0.05 mol) of 3-methoxy-4-benzenesulphonyloxy-acetophenone phenylhydrazone. Temperature and stirring were maintained for 20–30 minutes and the reaction medium was poured into water, after cooling to 80° C.

The indole derivative was extracted with ether and the ethereal phase was washed with water to neutrality, dried and concentrated under reduced pressure.

The precipitate which formed was recrystallized from methanol to give 2-(3'-methoxy-4'-benzenesulphonyloxy-phenyl)-indole.

Melting point: 156° C. Yield: 75%

By the same method but using the appropriate starting-products, the following compounds were prepared:

| Compound | Melting point | Yield |
|---|---|---|
| 2-(3',5'-dimethoxy-4'-benzenesulphonyloxy-phenyl)-indole | 150° C (ethanol) | 71% |
| 2-(3'-methoxy-4'-methylsulphonyloxy-phenyl)-indole | 194° C (methanol) | 70% |

EXAMPLE 11

2-(3'-Methoxy-4'-benzenesulphonyloxy-phenyl)-indole

Into a reactor equipped with a Dean-Stark separator were introduced 16.3 g (0.175 mol) of aniline and the reactor was heated to 180° C. While stirring, 17 g (0.05 mol) of 3-methoxy-4-benzenesulphonyloxy-ω-chloroacetophenone were added in 15 minutes. Stirring and temperature were maintained for 15 minutes and the reaction medium was poured into an aqueous solution of hydrochloric acid. The indole derivative was extracted with ether and the ethereal phase was washed with water to neutrality, dried and concentrated under reduced pressure.

After recrystallization from toluene 2-(3'-methoxy-4'-benzenesulphonyloxy-phenyl)-indole was obtained with a yield of 70%.

Melting point: 154° C.

EXAMPLE 12

2-(3'-Methoxy-4'-toluenesulphonyloxy-phenyl)-indole

Into a reactor were introduced 32.5 g (0.35 mol) of aniline. The reactor was heated to 180° C. and 35.5 g (0.1 mol) of molten 3-methoxy-4-toluenesulphonyloxy-ω-chloroacetophenone were added. The water which formed during the addition of the acetophenone was eliminated by distilling off the azeotrope water-aniline by means of a Dean-Stark separator. Stirring and a temperature of 180° C. were maintained for 15 minutes after the end of the operation of addition, and while stirring, the reaction medium was poured into 125 ml of water containing 25 ml of 36% hydrochloric acid.

Stirring was continued for 15 minutes and the indole derivative precipitated. The precipitate was suction-filtered, washed with water and triturated with 60 ml of methanol. The product was suction-filtered and dried to give 22 g of 2-(3'-methoxy-4'-toluenesulphonyloxy-phenyl)-indole.

Melting point: 182° C. Yield: 55.5%

EXAMPLE 13

2-(3'-Methoxy-4'-methylsulphonyloxy-phenyl)-indole

Into a reactor were introduced 65.1 g (0.7 mol) of aniline which was heated to 175°–180° C. and 55.7 g (0.2 mol) of molten 3-methoxy-4-methylsulphonyloxy-ω-chloroacetophenone were added in 15 minutes.

While stirring the water which formed was eliminated by means of a Dean-Stark separator and the temperature was maintained at 180° C. for 15 minutes after the end of the operation of addition.

While stirring, the reaction medium was poured into 500 ml of water containing 50 ml of 36% hydrochloric acid.

Stirring was continued for one hour and the mixture was extracted with toluene until complete dissolution of the precipitate.

The toluene solution was washed three times with water and dried over anhydrous sodium sulphate or by azeotropic distillation. The toluene solution was concentrated and the precipitate which formed was suction-filtered and dried to give 51 g of 2-(3'-methoxy-4'-methylsulphonyloxyphenyl)-indole.

Melting point: 194° C. Yield: 80%

EXAMPLE 14

2-(3'-Methoxy-4'-hydroxy-phenyl)-indole

Into a reactor were introduced 10 ml of water containing 4.8 g (0.12 mol) of solid sodium hydroxide, 30 ml of methanol and 7.58 g of 2-(3'-methoxy-4'-benzenesulphonyloxy-phenyl)-indole, prepared as in Examples 10 or 11, and, while stirring, the mixture was heated to 50°–55° C. for one hour.

The reaction medium was poured into an aqueous solution of hydrochloric acid and the indole derivative was extracted with ether.

The ethereal phase was washed with water to neutrality, dried, treated with charcoal and concentrated under reduced pressure.

After recrystallization from a toluene-ethanol mixture (90/10), 2-(3'-methoxy-4'-hydroxy-phenyl)-indole was obtained with a yield of 82%.

Melting point: 165° C.

By the same procedure but starting from 2-(3'-methoxy-4'-methylsulphonyloxy-phenyl)-indole, the same product as hereabove was obtained with a yield of 75%, whereas when starting from 2-(3'-methoxy-4'-toluenesulphonyloxy-phenyl)-indole a yield of 72% was obtained.

Finally, by the same method and using the appropriate starting-product, 2-(3',5'-dimethoxy-4'-hydroxy-phenyl)-indole was prepared with a yield of 80%.

Melting point: 230° C.

We claim:

1. A new acetophenone derivative of the general formula:

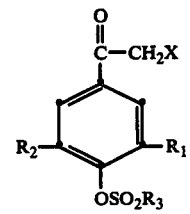

wherein X represents a hydrogen or halogen atom, $R_1$ and $R_2$, which are the same or different, each represent a hydrogen atom or a methoxy radical and $R_3$ represents an aryl radical, with the proviso that at least one of the substituents $R_1$ and $R_2$ is not a hydrogen atom.

2. A new compound according to claim 1 wherein X represents a chlorine or bromine atom.

3. A new compound according to claim 1 wherein $R_3$ represents a phenyl or p-tolyl radical.

4. 3-Methoxy-4-benzenesulphonyloxy-acetophenone.

5. 3-Methoxy-4-toluenesulphonyloxy-acetophenone.

6. 3,5-Dimethoxy-4-benzenesulphonyloxy-acetophenone.

7. 3-Methoxy-4-benzenesulphonyloxy-ω-chloroacetophenone.

8. 3-Methoxy-4-toluenesulphonyloxy-ω-chloroacetophenone.

9. 3-Methoxy-4-benzenesulphonyloxy-ω-bromoacetophenone.

* * * * *